(12) United States Patent
Robinson et al.

(10) Patent No.: US 8,551,456 B2
(45) Date of Patent: Oct. 8, 2013

(54) COMBINATION THERAPY AND METHODS FOR TREATING BACTERIAL BIOFILMS

(75) Inventors: Jayne Robinson, Dayton, OH (US); Tracy Collins, Medway, OH (US)

(73) Assignee: University of Dayton, Dayton, OH (US)

( * ) Notice: Subject to any disclaimer, the term of this patent is extended or adjusted under 35 U.S.C. 154(b) by 103 days.

(21) Appl. No.: 13/041,151

(22) Filed: Mar. 4, 2011

(65) Prior Publication Data

US 2011/0218139 A1  Sep. 8, 2011

Related U.S. Application Data

(60) Provisional application No. 61/310,868, filed on Mar. 5, 2010.

(51) Int. Cl.
| | |
|---|---|
| *A61K 31/409* | (2006.01) |
| *A61K 31/65* | (2006.01) |
| *A61K 31/7036* | (2006.01) |
| *A61K 38/14* | (2006.01) |
| *A61Q 11/00* | (2006.01) |

(52) U.S. Cl.
USPC ............. 424/49; 514/1.8; 514/2.4; 514/3.1; 514/36; 514/154; 514/185; 514/281; 514/410

(58) Field of Classification Search
None
See application file for complete search history.

(56) References Cited

PUBLICATIONS

Cassidy et al. Effect of sub-lethal challenge with Photodynamic Antimicrobial Chemotherapy . . . Journal of Photochemistry and Photobiology B: Biology. Feb. 11, 2010, vol. 99, pp. 62-66.*
Collins et al. The Effect of a Cationic Porphyrin on Pseudomonas aeruginosa Biofilms. Current Micrbiology. Apr. 6, 2010, vol. 61, pp. 411-416.*
Di Poto et al. The effect of photodynamic treatment combined with antibiotic action . . . Biomaterials. 2009, vol. 30, pp. 3158-3166.*
Donnelly et al. Delivery of photosensitisers and light through mucus . . . Jounral of Controlled Release. 2007, vol. 117, pp. 217-226.*
Mima et al. Susceptibility of Candida albicans to photodynamic therapy in a murine model of oral candidosis. Oral Surgery, Oral Medicine, Oral Pathology, Oral Radiology, and Endodontology. Mar. 1, 2010, vol. 109, pp. 392-401.*

* cited by examiner

*Primary Examiner* — Jeffrey E Russel
(74) *Attorney, Agent, or Firm* — Porter, Wright, Morris & Arthur LLP (57) ABSTRACT

A combination therapy for treating a bacterial biofilm comprises a therapeutically effective amount of an antibiotic comprising an aminoglycoside or tetracycline, or a combination of two or more thereof, and a cationic porphyrin in an amount effective for enhancing the effectiveness of the antibiotic in treating the bacterial biofilm. A method of treating a bacterial biofilm comprising *Pseudomonas aeruginosa* comprises contacting the bacterial biofilm with a combination therapy comprising a therapeutically effective amount of an antibiotic, and a cationic porphyrin in an amount effective for enhancing the effectiveness of the antibiotic in treating the bacterial biofilm. A method of treating a bacterial biofilm comprising *Pseudomonas aeruginosa* in a patient comprises administering to the patient a combination therapy comprising a therapeutically effective amount of an antibiotic, and a cationic porphyrin in an amount effective for enhancing the effectiveness of the antibiotic in treating the bacterial biofilm.

21 Claims, 5 Drawing Sheets

COMBINATION THERAPY AND METHODS FOR TREATING BACTERIAL BIOFILMS

RELATED APPLICATIONS

The present application claims priority under 35 U.S.C. §119 of U.S. Application No. 61/310,868 filed Mar. 5, 2010, incorporated herein in its entirety.

FIELD OF THE INVENTION

The present invention is directed to combination therapies for treating bacterial biofilms, particularly bacterial biofilms comprising *Pseudomonas aeruginosa*. The present invention is also directed to methods of treating such bacterial biofilms using the combination therapies.

BACKGROUND OF THE INVENTION

There is an urgent need to develop alternative therapies to replace or supplement current antibiotics for treating a whole spectrum of bacterial diseases in view of an alarming increase of antibiotic resistance that poses a very real threat to modern medicine. The emergence of resistant microbial strains, the nature of hospital environments, and the number of routine operations make the spread of infection more hazardous. Additionally, the ease and frequency of international travel assists in the spread of resistant bacteria throughout the world.

Many pathogenic microorganisms reside within biofilms which cause additional problems when designing new antimicrobial agents and therapies. A biofilm is an accumulation of microorganisms embedded in hydrated matrices of cells and containing polysaccharides, extracellular DNA, and proteases. Biofilms may form on solid biological or non-biological surfaces and account for a majority of microbial infections in the body. Bacteria growing in a biofilm rather than in free-floating forms tend to be particularly resistant to antimicrobial agents and it is often particularly difficult for a host immune system to render an appropriate response to bacterial biofilms.

Examples of biofilm-associated microbial infections include infections of oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents; cardiac implants such as pacemakers, prosthetic heart valves, ventricular assist devices, and synthetic vascular grafts and stents; prostheses, internal fixation devices, and percutaneous sutures; and tracheal and ventilator tubing. Both indwelling and subcutaneous biomedical implants or devices are potential sites for microbial infections and represent important targets for the control of infection, inflammation, and the immune response. Biomedical systems such as blood oxygenators, tracheal lavage, dental water units, and dialyzers are also susceptible to bacterial contamination and biofilm formation.

*Pseudomonas aeruginosa* (*P. aeruginosa*) is an opportunistic pathogen known to cause infections in immunocompromised individuals and is the leading cause of mortality among cystic fibrosis (CF) patients (10). The organism possesses a number of virulence factors that contribute to its ability to invade and colonize its host (19, 20) and typically resides in biofilms (5, 9, 13, 14, 23). *P. aeruginosa* has been shown to form biofilms on abiotic surfaces (e.g. catheters and stents) as well as biotic surfaces (e.g. urinary tract and lung tissue) (2, 7, 18). Biofilms are of significant medical importance because they confer the ability to organisms such as *P. aeruginosa* to evade the host immune system and render cells more resistant to antimicrobial agents (3, 15). These common characteristics lead to persistent and chronic infections (2).

Photodynamic therapy (PDT) has been useful in the treatment of certain cancers and other diseases such as macular degeneration. In recent years, there has been increased interest in using PDT as a means to treat bacterial infections (22). PDT requires three components: light, oxygen, and a photosensitizer. Light activated cationic porphyrins transfer energy to molecular oxygen resulting in the production of singlet oxygen ($^1O_2$). This mechanism is known as the Type II reaction. $^1O_2$ reacts with different components (e.g. phospholipids, peptides, and sterols) of the cell wall and cell membranes and also mediates DNA damage and cell death (21). The cationic porphyrin 5,10,15,20-tetrakis(1-methyl-pyridino)-21H,23H-porphine, tetra-p-tosylate salt (TMP), specifically causes DNA damage by intercalating between DNA base pairs, causing photoinduced strand breakage when irradiated (12, 16).

Previous studies have demonstrated the ability of cationic porphyrins to successfully photoinactivate Gram-positive and Gram-negative bacteria, as well as fungi (11). TMP at a concentration of 2.5 mg ml$^{-1}$ has been shown to reduce *P. aeruginosa* PAO1 planktonic cell populations by >$10^2$ cfu ml$^{-1}$ and higher concentrations (5.0 mg ml$^{-1}$) of TMP were necessary to achieve the same level of killing in bacteria enmeshed within biofilms (8). Additionally, TMP was shown to reduce *S. aureus* survival and, when combined with vancomycin, to disrupt established biofilms (6).

SUMMARY OF THE INVENTION

Accordingly, the present invention provides additional therapies for treatment of bacterial biofilms and, in specific embodiments, for treatment of bacterial biofilms comprising *P. aeruginosa*.

In one embodiment, the invention is directed to a combination therapy for treating a bacterial biofilm, comprising a therapeutically effective amount of an antibiotic comprising an aminoglycoside or tetracycline, or a combination of two or more thereof, and a cationic porphyrin in an amount effective for enhancing the effectiveness of the antibiotic in treating the bacterial biofilm.

In another embodiment, the invention is directed to a method of treating a bacterial biofilm comprising *P. aeruginosa*, the method comprising contacting the bacterial biofilm with a combination therapy comprising a therapeutically effective amount of an antibiotic, and a cationic porphyrin in an amount effective for enhancing the effectiveness of the antibiotic in treating the bacterial biofilm.

In a further embodiment, the invention is directed to a method of treating a bacterial biofilm comprising *P. aeruginosa*, in a patient, comprising administering to the patient a combination therapy comprising a therapeutically effective amount of an antibiotic, and a cationic porphyrin in an amount effective for enhancing the effectiveness of the antibiotic in treating the bacterial biofilm.

The present combination therapies and methods provide improved disruption of the bacterial biofilms which is advantageous in treating bacterial infection, i.e., killing bacteria. Importantly, the combination therapies and methods are operable without photoactivation of the porphyin, thereby providing treatment for infections in, inter alia, deep tissue that is not easily accessible to irradiation, such as lung biofilm infection in a cystic fibrosis patient.

These and additional objects, embodiments and advantages will be more fully discussed in the Detailed Description.

BRIEF DESCRIPTION OF THE DRAWINGS

Various aspects and embodiments of the invention are demonstrated in the Drawings, in which.

The Detailed Description provides further details of the Drawings.

DETAILED DESCRIPTION

The present invention is directed to combination therapies for treating bacterial biofilms, particularly bacterial biofilms comprising P. aeruginosa. The present invention is also directed to methods of treating such bacterial biofilms using the combination therapies. As used in the present specification, the term "combination therapy" refers to two or more therapeutic agents which are provided, applied and/or administered in association with one another. The combination therapy may comprise the two or more therapeutic agents in one formulation or in separate formulations. Separate formulations may, for example, be packaged in associated containers, although such is not required. Methods employing the combination therapy may apply or administer the two or more therapeutic agents simultaneously or sequentially, with sequentially encompassing a period of time between the respective applications or administrations. Such period of time may range from several seconds to several minutes to several hours or more.

The combination therapy comprises a therapeutically effective amount of an antibiotic, and a cationic porphyrin in an amount effective for enhancing the effectiveness of the antibiotic in treating the bacterial biofilm. As will be demonstrated below, the cationic porphyrin provides a non-photoactived disruption in the biofilm structure which allows the antibiotic to function more effectively against the bacteria within the biofilm. In one embodiment, the antibiotic is a gram negative bacteria antibiotic. Various antibiotics are suitable for use in the combination therapies, including, but not limited to, an aminoglycoside, glycopeptide or tetracycline, or a combination of two or more thereof. In specific embodiments, the antibiotic comprises an aminoglycoside and/or a glycopeptide. In additional embodiments, the antibiotic comprises tobramycin, vancomycin, gentamicin, kanamycin, and/or tetracycline.

Cationic porphyrins are known in the art and any of those known are suitable for use herein, including, but not limited to, tetra-substituted N-methyl-pyridyl-porphine (TMP), specifically, 5,10,15,20-tetrakis(1-methyl-pyridino)-21H,23H-porphine, including the tetra-p-tosylate salt; 5,10,15,20-tetra(N-methyl-4-pyridiniumyl)porphyrin (TMPyP); 5,10,15,20-tetra-(N-methyl-4-pyridyl)porphine (TMPyP4), and 5,10,15,20-tetra-(N-methyl-2-pyridyl)porphine (TMPyP2). The particular prophyrin TMP is highly water soluble and effective at low concentrations and does not appear to be toxic to human fibroblasts.

The methods according to the invention are particularly directed to treating bacterial biofilms which comprise P. aeruginosa. According to one embodiment, the methods comprise contacting the bacterial biofilm with a combination therapy comprising a therapeutically effective amount of an antibiotic as described above, and a cationic porphyrin as described above in an amount effective for enhancing the effectiveness of the antibiotic in treating the bacterial biofilm. The bacterial biofilm may be on an inanimate surface, or may be a living tissue surface. Additionally, the biofilm may be an inanimate surface implanted in living tissue. Examples include, but are not limited to, oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents; cardiac implants such as pacemakers, prosthetic heart valves, ventricular assist devices, and synthetic vascular grafts and stents; prostheses, internal fixation devices, and percutaneous sutures; and tracheal and ventilator tubing. When the biofilm is located in a patient, and not accessible in a noninvasive manner, the contact may be by administration to the patient. Thus, in this embodiment, the method comprises administering to the patient a combination therapy comprising a therapeutically effective amount of an antibiotic as described above, and a cationic porphyrin as described above in an amount effective for enhancing the effectiveness of the antibiotic in treating the bacterial biofilm. Administration may be in any suitable manner, including, but not limited to, oral, inhalation, topical, subcutaneous, parenteral, or the like.

In one specific embodiment, the bacterial biofilm is a lung biofilm in a cystic fibrosis patient. In another specific embodiment, the bacterial biofilm is on one or more teeth of a patient. In another embodiment of the present invention, the combination therapy is applied to a subject as a topical agent for burns, eye and/or skin infections.

As will be demonstrated in the following examples, the contact and/or administration may be effected with or without photoactivation of the porphyrin. Importantly, the prophyrin provides enhanced effectiveness of the antibiotic, even in the absence of photoactivation. Thus, the present methods are particularly advantageous for treatment of biofilms which are located in areas, e.g., deep tissue, where photoactivating irradiation is difficult to provide. If the porphyrin is photoactivated, additional therapeutic effect may be obtained. Any suitable light source may be used to photoactivate the porphyrin in such embodiments, including low energy sources as laser light is not required.

The combined effect of the porphyrin and the antibiotic is significantly higher than either alone. Further, bacteria are unlikely to develop resistance to the porphyrin as its mechanism of action is to act outside of the cell on the DNA in the extracellular matrix of a biofilm or to generate singlet oxygen which targets virtually all cellular components. In particular, the mechanism of the present invention can be different from traditional antibiotics: (1) photoactivation generates singlet oxygen which destroys most biomolecules very rapidly, and (2) without photoactivation, the porphyrin intercalates into extracellular DNA and it is unlikely that microbes would modify the structure of their DNA to avoid this—indeed there is no evidence that organisms have developed a way to avoid intercalating agents from intercalating into their DNA.

Thus, one embodiment of this invention uses a compound that is non-toxic but previously thought to only be effective at killing bacteria when activated by light. The invention employs a mechanism not requiring photoactivation and bacteria in biofilms are killed by disrupting the biofilm structure. The target is the extracellular DNA within the biofilm matrix. Intercalation of the porphyrin into the biofilm DNA results in an unwinding of the DNA which renders the biofilm more permeable to antibiotics. The DNA in the biofilm of this embodiment represents a novel target for antimicrobial compounds and a way to actually remove the biofilm from the substratum in addition to killing individual cells. Thus, it can be delivered to infections deep within tissues where photodynamic therapy has failed.

EXAMPLES

Example 1

Bacterial Strains, Growth Conditions and Chemicals

*P. aeruginosa* PAO1 wild-type and isogenic pqsA mutant strain were obtained from Eb Pesci (East Carolina University School of Medicine). *P. aeruginosa* strains were grown aerobically with shaking in Minimal Salts medium (40 mM $K_2HPO_4$, 20 mM $KH_2PO_4$, 7.6 mM $[NH_4]_2SO_4$, 0.2 mM $MgSO_4.7H_2O$, $9.2 \times 10^{-3}$ mM $FeCl_3.6H_2O$, 0.2% [wt/vol] glucose; adjusted pH 7.0) at 37° C. (4, 17). For static biofilms, *P. aeruginosa* strains were grown overnight in Minimal Salts medium at 37° C. with shaking. The following day, bacteria were diluted in fresh media to an $OD_{590nm}$ of 0.15. Five hundred microliters of the standardized culture was added to sterile polystyrene cuvettes and incubated statically for 24 h at 37° C. For examination of static biofilms using confocal laser scanning microscopy (CSLM), sterile microscope slides were submerged in standardized cell suspensions and incubated statically at 37° C. for 24 h.

Photosensitizer.

5,10,15,20-tetrakis(1-methyl-pyridino)-21H,23H-porphine, tetra-p-tosylate salt (TMP) was purchased through Sigma-Aldrich. A 12.5 mg ml-1 TMP stock solution was prepared in deionized $H_2O$ and filter sterilized. TMP was added to cell suspensions and biofilms at various concentrations. TMP concentrations of 100 (0.14 mg ml$^{-1}$) and 225 µM (0.14 mg ml$^{-1}$) were chosen based on their effectiveness in preliminary trials.

Photoactivation.

TMP was activated using a 100-Watt mercury vapor lamp fitted with a colored glass filter (Newport FSR-GG420) blocking wavelengths shorter than 400 nm. Samples were irradiated for various exposure times at an intensity of 192 Joules/$cm^2$.

CSLM of Static Biofilms.

Overnight biofilms formed on slides were rinsed in phosphate buffered saline (PBS), pH 7.0, and transferred to 50 ml tubes containing PBS supplemented with TMP at a concentration of either 100 or 225 µM. Negative control slides were transferred to 50 ml tubes containing only PBS. Following pre-exposure to TMP, biofilms were irradiated for 10 min and washed briefly in PBS. Bacterial viability was assessed in biofilm cultures using the LIVE/DEAD BacLight bacterial viability assay (Molecular Probes Inc., Eugene, Oreg.), containing SYTO9 and propidium iodide dyes. Biofilms were visualized with an Olympus FV1000 CSLM (Olympus America, Center Valley, Pa.) using a 60× oil immersion objective. Biofilm images were acquired in 0.4 µm optical sections for the entire thickness of the biofilm.

Effect of TMP on Viability of Biofilm Associated Cells.

Static biofilms formed in sterile polystyrene cuvettes, as described above, were used to quantify cell survival. Supernatants from 24 h biofilms were removed and replaced with PBS containing TMP and irradiated for 10 min. Cells released from the biofilm following treatment were collected from the supernatant by centrifugation and resuspended in PBS. The remaining attached biofilm was washed once and resuspended in PBS. The number of viable cells in the supernatant and attached biofilms following treatment were determined by plating on LB (1.5% agar) plates that were incubated for 24 h at 37° C.

TMP Effects on Biofilm Structure and Cell Viability.

Figure 1:
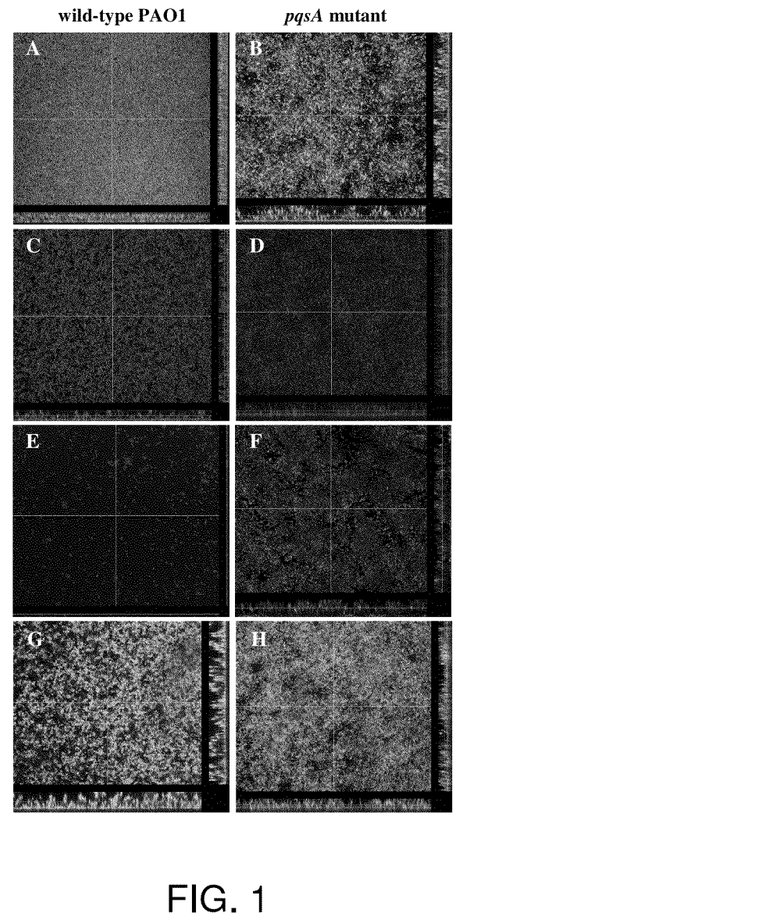
FIG. 1 presents panels A-H showing confocal scanning laser micrographs of P. aeruginosa biofilms as described in Example 1.

The effect of TMP on 24 h *P. aeruginosa* PAO1 biofilms was assessed using CSLM and viable plate counts. FIG. 1 shows confocal scanning laser micrographs of the *P. aeruginosa* biofilms which were grown on glass slides for 24 h under static conditions in MSM and then exposed to specified concentrations of TMP. Following exposure to TMP, the biofilms were either irradiated (panels A-F) with a 100-Watt mercury vapor lamp for 10 min or incubated without photoactivation, i.e., in the dark (panels G and H). Bacterial viability was determined using the LIVE/DEAD BacLight Bacterial Viability assay. The cells in panels C-F show significant staining in red (considered dead) while cells in panels A, B, G and H show predominate staining in green (alive). The images show horizontal optical sections from the midpoint of the biofilms flanked by vertical optical sections in biofilms treated with: (panels A-B), No TMP, light; (panels C-D), 100 µM TMP, light; (panels E-F), 225 µM TMP, light; and (panels G-H), 225 µM TMP, dark. In the absence of TMP, wild-type PAO1 cells formed dense biofilms on glass slides (panel A) and in polystyrene cuvettes (data not shown). When wild-type PAO1 biofilms were exposed to 100 µM TMP and irradiated for 10 min, there was a decrease in biofilm density and the majority of cells within the biofilm were non-viable based on LIVE/DEAD staining (panel C). Exposure to 225 µM TMP and 10 min of irradiation resulted in a nearly complete disruption and clearance of established wild-type PAO1 biofilms (panel E). The few remaining attached cells were nonviable. Shorter periods of light exposure or lower concentrations of TMP resulted in less clearance of the biofilms (data not shown). Interestingly, biofilms exposed to TMP but not irradiated appeared to be expanded in volume without a loss of cell viability (panel G).

Figure 2:
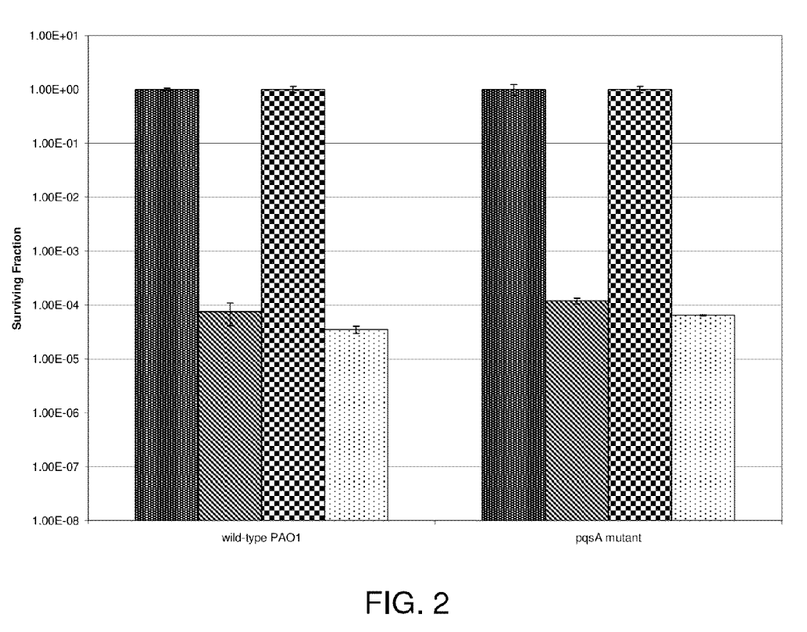
FIG. 2 graphically presents the effect of TMP and light irradiation on cell survival of P. aeruginosa biofilm-associated cells as described in Example 1.

Standard plate counts of cells recovered from biofilms formed in polystyrene cuvettes were used to quantify the effects of photoactivated TMP. FIG. 2 shows the effect of TMP and light irradiation on cell survival of *P. aeruginosa* biofilm associated cells. Established biofilms of wild-type PAO1 and the pqsA mutant were treated with TMP and irradiated 10 min with a 100-Watt mercury vapor lamp as described. Cells were collected from the supernatant of treated biofilms, as well as from the remaining attached biofilm. Cell suspensions were diluted and plated onto LB (1.5% agar) plates and incubated 24 h at 37° C. CFU were used to determine the surviving fraction. In FIG. 2, Attached cells: no TMP▨, 225 µM TMP▨; Supernatant cells: no TMP▨, 225 µM TMP▨. Wild-type biofilms exposed to 225 µM TMP and 10 min of irradiation exhibited a 4.1-$\log_{10}$ decrease in viable cells in the attached biofilm population (FIG. 2). There was a 4.5-$\log_{10}$ reduction in the number of viable cells in the recovered supernatants of wild-type PAO1 biofilms following the same TMP treatment (FIG. 2). The recovered supernatants contained the cells sloughed off as the result of TPM exposure and irradiation.

In contrast to wild-type biofilms, pqsA mutant biofilms were significantly different in overall structure. As previously noted, these biofilms are not confluent (1) (FIG. 1, panel B). When exposed to 100 or 225 µM TMP and irradiated for 10 min there was a decrease in cell viability of attached cells (FIG. 1, panels D and F). Standard plate counts of attached cells showed a 3.9-$\log_{10}$ decrease in cell viability at TMP concentrations of 225 µM (FIG. 2). Similarly, there was a 4.2-$\log_{10}$ reduction in cell viability of pqsA cells collected from supernatants of irradiated biofilms treated with 225 µM TMP (FIG. 2). Although exposure to TMP and irradiation resulted in cell death, this treatment did not lead to the disruption or clearance of the pqsA mutant biofilms observed with wild-type cells. Without photoactivation, TMP did not affect cell viability or disrupt the architecture of pqsA mutant biofilms (FIG. 1 panel H).

The present example examines the effects of the cationic porphyrin, TMP, on established *P. aeruginosa* biofilms. TMP exposure plus photoactivation resulted in a substantial reduction in the numbers of viable bacteria within established wild-type *P. aeruginosa* biofilms as shown by viability staining (FIG. 1 panels C and E) and standard plate counts (FIG. 2). Bacterial killing required photoactivation, indicating that there was no dark toxicity associated with TMP (FIG. 1 panel G).

Previous studies have demonstrated that TMP at higher concentrations (5.0 mg ml$^1$) than used in this study resulted in a 1.2-$\log_{10}$ reduction of wild-type PAO1 isolates grown in biofilms when irradiated for 5 min (8). The present examples were able to achieve higher rates of killing (4.1-$\log_{10}$ reduction) of biofilm associated wild-type PAO1 cells using concentrations of TMP as low as 0.32 mg ml$^{-1}$ (225 µM) (FIG. 2). This difference in killing rates can be attributed to the different conditions under which the established biofilms were grown and treated.

Previous studies did not evaluate the change in *P. aeruginosa* biofilm structure following treatment with TMP and light. In addition to killing biofilm-associated bacteria, treatment with TMP followed by irradiation resulted in substantial disruption and clearance of wild-type PAO1 biofilms (FIG. 1 panels C and E). At a concentration of 225 µM TMP, wild-type biofilms were completely disrupted with few cells remaining attached (FIG. 1 panel E). Without photoactivation, TMP did not lead to clearance of wild-type biofilms; however, there was a noticeable expansion in the biofilm and loss of density (FIG. 1G). These results indicate that TMP photoactivation affects biofilms in two ways: direct killing of cells and the disruption of the biofilm architecture. Additionally, while TMP toxicity is dependent on photoactivation, it is able to alter biofilm architecture in the absence of light by an unknown mechanism.

Example 2

TMP Induced Degradation of DNA.

pUC18 plasmid DNA (100 ng ml-1) was incubated with TMP at a final concentration of 100 or 225 µM. Plasmid DNA with and without TMP was irradiated for designated times. Prior to light exposure, samples of DNA supplemented with TMP were collected and incubated in the dark for comparison. DNA was examined using agarose gel electrophoresis.

DNA Degradation in the Presence of TMP.

Figure 3:
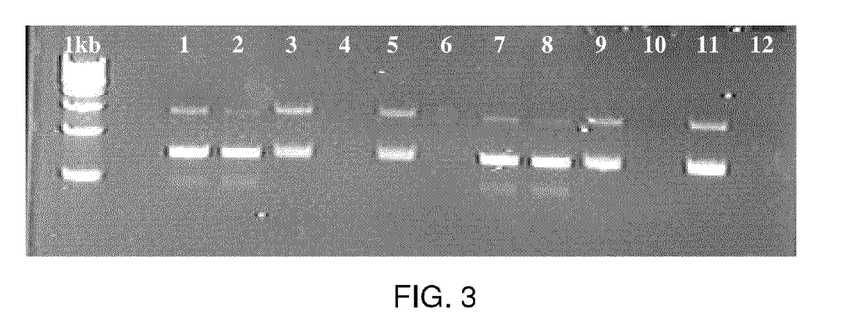
FIG. 3 shows gel electrophoresis analysis of plasmid (pUCP18) DNA treated with TMP and, in certain instances, irradiated, as described in Example 2.

To determine the effect of TMP on DNA, pUCP18 plasmid DNA was exposed to TMP and irradiated as described. FIG. 3 shows the gel electrophoresis analysis of the pUCP18 plasmid DNA treated with TMP and irradiated. Purified plasmid (pUCP18) DNA (100 ng ml$^{-1}$) was exposed to either 0, 100 or 225 µM TMP and irradiated with a 100-Watt mercury vapor lamp for 0, 5, or 30 min, as follows: Lane 1: 0 TMP, nonirradiated control DNA; Lane 2: 0 TMP, irradiated 5 min, Lane 3: 100 µM TMP, nonirradiated, Lane 4: 100 µM TMP, irradiated 5 min, Lane 5: 225 µM TMP, nonirradiated, Lane 6: 225 µM TMP, irradiated 5 min, Lane 7: 0 TMP, nonirradiated, Lane 8: 0 TMP, irradiated 30 min, Lane 9: 100 µM TMP, nonirradiated, Lane 10: 100 µM TMP, irradiated 30 min, Lane 11: 225 µM TMP, nonirradiated, and Lane 12: 225 µM TMP, irradiated 30 min. The untreated control samples had the three expected forms of plasmid DNA: covalently closed circles, relaxed circular, and linear cut (FIG. 3: lanes 1 and 7). Plasmid DNA exposed to light only appeared similar to the control (FIG. 3: lanes 2 and 8).

Plasmid DNA treated with 100 or 225 µM TMP without subsequent photoactivation resulted in retarded migration of DNA (FIG. 3: lanes 3, 5, 9, and 11) as expected due to its ability to intercalate into DNA (12, 16). The combination of TMP and irradiation for either 5 or 30 min resulted in the complete degradation of pUCP18 plasmid DNA at concentrations of 100 or 225 µM TMP (FIG. 3: lanes 4, 6, 10, and 12).

To determine if disruption of established *P. aeruginosa* wild-type biofilms was solely due to inactivation of biofilm associated cells or also involved the extracellular matrix of the biofilm, the effects of TMP on extracellular DNA were also examined. Extracellular DNA has previously been shown to be necessary for normal biofilm formation and contributes to the overall architecture (23). Extracellular DNA in biofilms was quantified following treatment with TMP and photoactivation compared with untreated biofilms using various DNA stains, such as Pico Green. A decrease was observed in biofilm DNA of samples treated with TMP and light but there was also a decrease in biofilm DNA of samples that were treated with TMP in the absence of light (data not shown). Because both TMP and Pico Green intercalate between base pairs, it was not possible to determine using Pico Green if this decrease in fluorescence was proportional to a reduction in extracellular biofilm matrix DNA or due to competitive inhibition, i.e., the intercalation of TMP preventing binding of Pico Green.

Due to the difficulty in quantifying extracellular biofilm DNA following TMP exposure using established staining techniques, the effects of TMP on purified pUCP18 DNA and a pqsA mutant were assessed. Prior to irradiation, pUCP18 plasmid DNA migration was retarded following exposure to TMP, indicating intercalation of TMP (FIG. 3, lanes 3, 5, 9, and 11). Exposure to TMP and subsequent photoactivation led to complete degradation of pUCP18 plasmid DNA (FIG. 3, lanes 4, 6, 10, and 12). These results coincide with previous studies that demonstrated that TMP intercalates between DNA base pairs, causing photocleavage of DNA (12, 16). Thus, TMP is expected to intercalate into available extracellular DNA within biofilms and, upon irradiation, lead to disruption of the DNA. Degradation of extracellular DNA in the biofilm matrix using DNase has been previously shown to disrupt biofilm architecture and lead to the dissolution of the biofilm (23). TMP photocleavage of DNA would similarly result in the disruption of biofilms.

The pqsA mutant, defective in a late portion of the *P. aeruginosa* quorum-sensing system, has been shown to produce biofilms with substantially lower levels of extracellular DNA (1). In the presence of TMP and light, high levels of killing were observed in pqsA mutant biofilms (FIG. 1 panels D and F). However, in contrast to wild-type biofilms, the biofilms formed by the pqsA mutant were not disrupted by this treatment. The inability of TMP photoactivation to disrupt pqsA biofilms could be attributed, in part, to the lack of extracellular DNA in these biofilms. It appears that disruption of *P. aeruginosa* PAO1 wild-type biofilms by TMP and light treatment is partially due to its effect on the extracellular DNA matrix and not just photoinactivation of the cells within the matrix. However, the lack of dissolution of pqsA mutant biofilms by TMP photoactivation may not be solely due to differences in DNA content as these biofilms differ from wild-type biofilms in a number of important ways.

Example 3

Combined TMP and Tobramycin Treatment.

Biofilms were grown on glass slides as described above. The 24 h biofilms were incubated for 10 min in 225 µM TMP, rinsed in PBS and transferred to tubes containing MSG or MSG supplemented with 100 µg ml$^{-1}$ of tobramycin. Slides were incubated in tobramycin for 2 h at 37° C. All incubations were performed in the dark. Cell viability within biofilms was assessed using the LIVE/DEAD BacLight bacterial viability kit and visualized with an Olympus FV1000 CSLM as described above.

Effect of Tobramycin on TMP Treated Biofilms.

Figure 4:
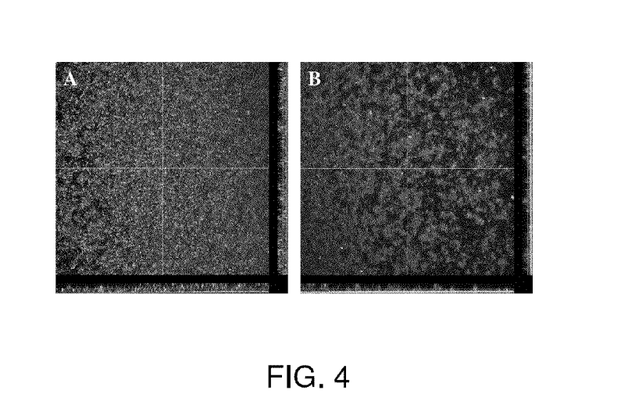
FIG. 4 presents panels A and B showing confocal scanning laser micrographs of P. aeruginosa biofilms as described in Example 3.

Wild-type PAO1 biofilms were exposed to TMP for 10 min followed by exposure to 100 µg ml-1 of tobramycin for 2 h with all steps performed in the dark, i.e., without photoactivation of the TMP. FIG. 4 shows confocal scanning laser micrographs of *P. aeruginosa* wild-type PAO1 biofilms treated with tobramycin only and TMP and tobramycin in the absence of light. As described above, biofilms were grown on glass slides for 24 h at 37° C. and then exposed to TMP (225 µM) for 10 min in the dark. Following exposure to TMP, biofilms were incubated with tobramycin (100 µg ml$^{-1}$) for 2 h at 37 C. Bacterial viability was determined using the LIVE/DEAD BacLight Bacterial Viability assay. The images show horizontal optical sections from the midpoint of the biofilms flanked by vertical optical sections in biofilms treated with panel A showing tobramycin alone and panel B showing TMP+tobramycin. In FIG. 4, panel A shows cells predominately staining green (alive), with a small amount of cells staining red (dead), while panel B shows a predominate amount of cells staining red (dead).

As noted above, TMP treatment without photoactivation resulted in an expansion and loss of biofilm density with no observable reduction in cell viability. In biofilms treated with tobramycin there was a reduction in cell viability which was limited to cells near the surface of the biofilms, where oxygen is most plentiful (FIG. 4 panel A). Treatment with TMP and subsequent exposure to tobramycin resulted in substantial clearance of the biofilms and greater loss of cell viability throughout the biofilms than with either single treatment (FIG. 4 panel B).

The ability of TMP to intercalate into DNA, leading to an unwinding and expansion of the DNA volume, may explain the expansion of wild-type PAO1 biofilms treated with TMP but not exposed to light. This change in the architecture of *P. aeruginosa* biofilms treated with TMP in the absence of photoactivation affects the ability of antibiotics to kill bacteria within biofilms. The combined effects of TMP and the antibiotic tobramycin, without photoactivation, i.e., in the dark, were examined on established biofilms as described above. Treatment of wild-type PAO1 biofilms with tobramycin, the major front-line antibiotic used in the treatment of cystic fibrosis (CF) lung disease, did not result in substantial biofilm clearance and led to minimal killing of biofilm associated cells (FIG. 4 panel A). Killing was primarily localized to the top layer of the biofilm. In contrast, exposure of wild-type PAO1 biofilms to TMP prior to treatment with tobramycin resulted in significant biofilm clearance and enhanced killing of cells (FIG. 4 panel B).

Example 4

Using the same protocol used in Example 3 for tobramycin, additional antibiotics were tested to aid in the elucidation of the mechanism of bacterial biofilm disruption in the absence of photoactivation. Table 1 shows antibiotics tested and their respective mechanism of action.

TABLE 1

Effect of antibiotics with different modes of action on *P. aeruginosa* biofilm cells

| Target | Mode of Action | Antibiotic | TMP + Antibiotic pH 4 | TMP + Antibiotic pH 7 |
|---|---|---|---|---|
| cell wall | inhibits cell wall synthesis by preventing cross-linking of peptidoglycan (PG) strands | carbenicillin | ND | − |
| | inhibits cell wall synthesis by preventing transglycosylation step in PG polymerization | vancomycin | ND | +++ |
| DNA | fluoroquinolones - inhibits DNA synthesis | Ciprofloxacin | ND | + |
| protein | aminoglycoside - inhibits protein synthesis binds to 30S preventing formation of ribosome | gentamicin | ND | ++ |
| | aminoglycoside - inhibits protein synthesis binds to 30S preventing formation of ribosome | kanamycin | ND | + |
| | aminoglycoside - inhibits protein synthesis binds to 30S preventing formation of ribosome | tobramycin | +++ | ++++ |
| | inhibits protein synthesis binds to 30S preventing tranfer of a.a. to ribosome | tetracycline | ND | +/− |

ND = not determined;
(−) = no killing;
(+) = killing

Figure 5A:
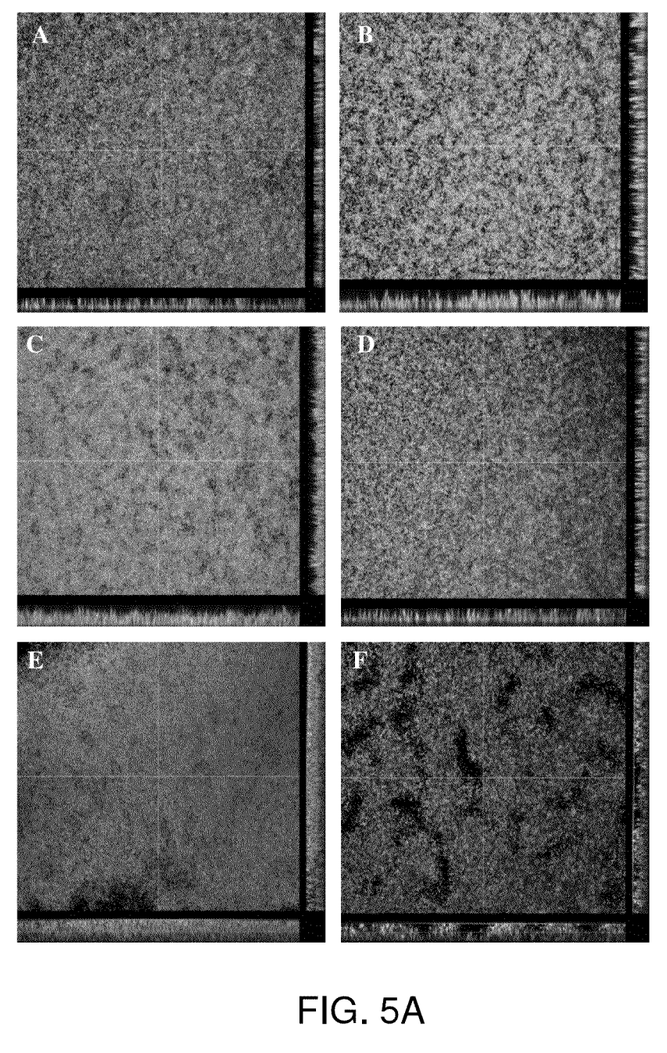
FIGS. 5A and 5B present panels A-N showing confocal scanning laser micrographs of P. aeruginosa biofilms as described in Example 4.
Figure 5B:
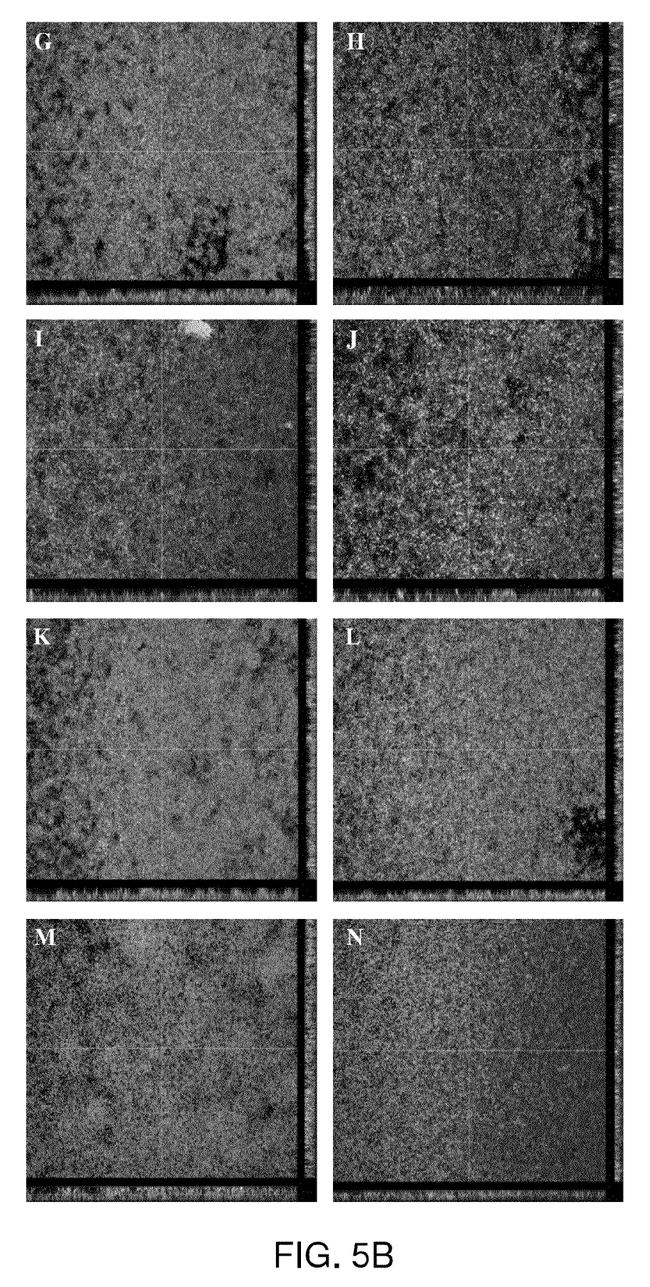

FIGS. 5A and 5B present confocal scanning laser micrographs of *P. aeruginosa* wild-type PAO1 biofilms treated with TMP versus TMP plus antibiotic in the absence of light. Biofilms were grown on glass slides for 24 h at 37° C. and then exposed to TMP (225 µM) for 10 min without photoactivation, i.e., in the dark. Following exposure to TMP, the biofilms were incubated with the respective antibiotic listed below (100 µg ml$^{-1}$) for 2 h at 37 C. Bacterial viability was determined using the LIVE/DEAD BacLight Bacterial Viability assay. Cells staining red are considered dead while cells staining green are alive. The panels show horizontal optical sections from the midpoint of the biofilms flanked by vertical optical sections in biofilms treated with: (A, B)=no antibiotic (control), TMP only (control); (C, D)=carbenicilin (Cb), Cb+TMP; (E, F)=vancomycin (Vm), Vm+TMP; (G, H)=ciprofloxacin (Cf), Cf+TMP; (I, J)=Gentimycin (Gm), Gm+TMP; (K, L)=Kanamycin (Km), Km+TMP; (M, N)=tetracycline (Tc), Tc+TMP. In summary, panels C, E, G, I, K and M received the respective antibiotic alone, and panels B, D, F, H, J, L and N were treated with the combination of TMP and antibiotic. Panels D and H showed little or no increase in red staining, panels J, L and N showed significant increased red staining, and Panel F showed predominately red staining.

As shown in FIG. 5B, panels G and H, the antibiotic ciprofloxacin, which works by inhibiting DNA synthesis, had no gain in killing by the addition of TMP to the antibiotic. This supports the hypothesis that the mechanism by which TMP enhances the effect of antibiotics is via intercalation into extracellular DNA. Two different cell wall synthesis inhibitors, carbenicillin and vancomycin (FIG. 5A, panels C, D and E, F, respectively) were tested. There was no enhanced killing with the addition of TMP to carbenicillin. In contrast, TMP substantially enhanced killing by vancomycin. This was unanticipated as vancomycin is not purportedly effective against gram-negative bacteria such as *P. aeruginosa*. All the antibiotics that acted by the same mechanism as tobramycin i.e., gentamycin, kanamycin and tetracycline (FIG. I-N), behaved similarly to tobramycin. The combined results of these trials with the different antibiotics suggests that the dark (non-photoacitvated) mechanism of TMP does involve DNA but also protein synthesis. Importantly, vancomycin may be effective against gram-negative bacteria when used in combination with TMP. Additionally, the effect of pH on the combination of tobramycin and TMP under dark conditions was tested. An enhancement of killing was seen when a combination of TMP and antibiotic was used in a pH range of 4.0 to 8.0.

One of the limitations of photodynamic therapy is the delivery of light to infections in deep tissue. The present findings are especially important because they show that TMP can act to disrupt biofilm structure when activated by light and also by a light independent mechanism that enhances killing when combined with tobramycin. A light independent treatment has the potential to be applied when trying to eradicate *P. aeruginosa* biofilms that are not easily accessible to irradiation such as those associated with cystic fibrosis patients.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

REFERENCES

1. Allesen-Holm M, Barken K B, Yang L, et al. (2006) A characterization of DNA release in *Pseudomonas aeruginosa* cultures and biofilms. Mol Microbiol 59:1114-1128.
2. Costerton J W, Stewart P S, Greenberg E P (1999) Bacterial biofilms: a common cause of persistent infections. *Science* 284:1318-1322.
3. Costerton, J W (2001) Cystic fibrosis pathogenesis and the role of biofilms in persistent infection. *Trends Microbiol* 9:50-52.
4. Craven, R C, Montie T C (1983) Chemotaxis of *Pseudomonas aeruginosa*: Involvement of Methylation. *J Bacteriol* 154:780-786.
5. D'Argenio D A, Calfee M W, Rainey P B, et al. (2002) Autolysis and autoagreggation of *Pseudomonas aeruginosa* colony morphology mutants. *J Bacteriol* 184:6481-6489.
6. Di Poto A, Sbarra M S, Provenza G, et al. (2009) The effect of photodynamic treatment combined with antiobiotic action or host defence mechanism on *Staphylococcus aureus* biofilms. *Biomaterials* 30:3158-3166.
7. Donlan, R M, Costerton J W (2002) Biofilms: Survival Mechanisms of Clinically Relevant Microorganisms. *Clin Microbiol Rev* 15:167-193.
8. Donnelly R F, McCarron P A, Cassidy C M, et al. (2007) Delivery of photosensitisers and light through mucus: Investigations into the potential use of photodynamic therapy for treatment of *Pseudomonas aeruginosa* cystic fibrosis pulmonary infection. *J Controlled Release* 117: 217-226.
9. Freidman L, Kolter R (2004) Genes involved in matrix formation in *Pseudomonas aeruginosa* PA14 biofilms. *Mol Microbiol* 51:675-690.
10. Govan J R, Deretic V (1996) Microbial pathogenesis in cystic fibrosis: mucoid *Pseudomonas aeruginosa* and *Burkholderia cepacia*. *Microbiol Rev* 60:539-574.
11. Hamblin M R, Hasan T (2004) Photodynamic therapy: a new antimicrobial approach to infectious disease. *Photochem Photobiol Sci* 3:436-450.
12. Kelly J M, Murphy M J (1985) A comparative study of the interaction of 5,10,15,20-tetrakis(N-methylpyridinum-4-yl)porphyrin and its zinc complex with DNA using fluorescence spectroscopy and topoisomerisation. *Nucleic Acids Res* 13:167-184.
13. Matsukawa M, Greenberg E P (2004) Putative exopolysaccharide synthesis genes influence *Pseudomonas aeruginosa* biofilm development. *J Bacteriol* 186: 4449-4456.
14. Nemoto K, Hirota K, Mukarami K, et al. (2003) Effect of Varidase (streptodornase) on biofilm formed by *Pseudomonas aeruginosa*. *Chemotherapy* 49:121-125.
15. Nickel J C, Ruseska I, Wright J B, et al. (1985) Tobramycin resistance of *Pseudomonas aeruginosa* cells growing as a biofilm on urinary tract catheter. *Antimicrob Agents Chemother* 27:619-624.
16. Pasternack R F, Gibbs E J (1996) Porphyrin and metalloporphyrin interactions with nucleic acids. *Met Ions Biol Syst* 33:367-397.
17. Sambrook J, Fritsch E F, Maniatis T (1989) *Molecular cloning: a laboratory manual*. 2$^{nd}$ Edition. Cold Spring Harbor Laboratory Press, Cold Spring Harbor, N.Y.
18. Speer A G, Cotton P B, Rode J, et al. (1988) Biliary stent blockage with bacterial biofilm. A light and electron microscopy study. Ann Intern Med 108:546-553.
19. van Delden C, Iglewski B H (1998) Cell-to-cell signaling and *Pseudomonas aeruginosa* infections. *Infect Dis* 4: 551-560.
20. van Delden C (2004) Virulence factors in *Pseudomonas aeruginosa*. In: Ramos J-L, edn. *Pseudomonas*: virulence and gene regulation. New York, Kluwer Academic/Plenum Publishers, pp 3-45.

21. Wainwright M (1998) Photodynamic antimicrobial chemotherapy (PACT). *J Antimicrob Chemother* 42:13-28.
22. Wainwright M (2009) Photoantimicrobials—So what's stopping us? *Photodiag Photodyn Ther* 6:167-169.
23. Whitchurch C B, Tolker-Nielsen T, Ragas P C, et al. (2002) Extracellular DNA is required for bacterial biofilm formation. *Science* 295:1487.

What is claimed is:

1. A formulation for treating a bacterial biofilm, comprising a therapeutically effective amount of an antibiotic comprising an aminoglycoside or tetracycline, or a combination of two or more thereof, and a cationic porphyrin in an amount effective for enhancing the effectiveness of the antibiotic in treating the bacterial biofilm.

2. The formulation of claim 1, wherein the antibiotic comprises an aminoglycoside.

3. The formulation of claim 1, wherein the cationic porphyrin comprises 5,10,15,20-tetrakis(1-methyl-pyridino)-21H,23H-porphine, tetra-p-tosylate salt (TMP).

4. The formulation of claim 3, wherein the antibiotic comprises tobramycin.

5. A method of treating a bacterial biofilm comprising *Pseudomonas aeruginosa*, comprising contacting the bacterial biofilm with a therapeutically effective amount of an antibiotic, and a cationic porphyrin in an amount effective for enhancing the effectiveness of the antibiotic in treating the bacterial biofilm.

6. The method of claim 5, wherein the method is conducted without photoactivation of the cationic porphyrin.

7. The method of claim 5, wherein the cationic porphyrin is photoactivated.

8. The method of claim 5, wherein the antibiotic comprises an aminoglycoside, glycopeptide or tetracycline, or a combination of two or more thereof.

9. The method of claim 5, wherein the cationic porphyrin comprises 5,10,15,20-tetrakis(1-methyl-pyridino)-21H,23H-porphine, tetra-p-tosylate salt (TMP).

10. The method of claim 9, wherein the antibiotic comprises tobramycin and/or vancomycin.

11. A method of treating a bacterial biofilm comprising *Pseudomonas aeruginosa* in a patient, comprising administering to the patient a therapeutically effective amount of an antibiotic, and a cationic porphyrin in an amount effective for enhancing the effectiveness of the antibiotic in treating the bacterial biofilm.

12. The method of claim 11, wherein the bacterial biofilm is a lung biofilm of a cystic fibrosis patient.

13. The method of claim 11, wherein the bacterial biofilm is on one or more teeth of the patient.

14. The method of claim 11, wherein the method is conducted without photoactivation of the cationic porphyrin.

15. The method of claim 11, wherein the antibiotic comprises an aminoglycoside, glycopeptide or tetracycline, or a combination of two or more thereof.

16. The method of claim 11, wherein the antibiotic comprises an aminoglycoside and/or a glycopeptides.

17. The method of claim 11, wherein the cationic porphyrin comprises 5,10,15,20-tetrakis(1-methyl-pyridino)-21H,23H-porphine, tetra-p-tosylate salt (TMP).

18. The method of claim 17, wherein the antibiotic comprises tobramycin or vancomycin.

19. The method of claim 17, wherein the antibiotic comprises tobramycin.

20. The method of claim 11, wherein the antibiotic and cationic porphyrin are administered sequentially.

21. The method of claim 11, wherein the antibiotic and cationic porphyrin are administered simultaneously.

* * * * *